United States Patent
Tsai et al.

(10) Patent No.: US 11,969,518 B2
(45) Date of Patent: Apr. 30, 2024

(54) ARTIFICIAL DRESSING AND USE OF ARTIFICIAL DRESSING FOR PROMOTING WOUND HEALING

(71) Applicant: A.M.S. BioteQ Co., Ltd., Kaohsiung (TW)

(72) Inventors: Yi-Ju Tsai, Kaohsiung (TW); Ying-Ting Yeh, Kaohsiung (TW); Meng-Yi Bai, Taipei (TW); Yun-Xuan Zhang, Changhua County (TW)

(73) Assignee: A.M.S. BioteQ Co., Ltd., Kaohsiung (TW)

( * ) Notice: Subject to any disclaimer, the term of this patent is extended or adjusted under 35 U.S.C. 154(b) by 0 days.

(21) Appl. No.: 17/879,797

(22) Filed: Aug. 3, 2022

(65) Prior Publication Data
US 2024/0042096 A1   Feb. 8, 2024

(51) Int. Cl.
*A61L 26/00* (2006.01)
*A61K 36/07* (2006.01)
*A61P 17/02* (2006.01)

(52) U.S. Cl.
CPC .......... *A61L 26/0066* (2013.01); *A61K 36/07* (2013.01); *A61L 26/0038* (2013.01); *A61L 26/0085* (2013.01); *A61P 17/02* (2018.01); *A61L 2300/30* (2013.01)

(58) Field of Classification Search
CPC .................................................. A61L 26/0066
See application file for complete search history.

(56) References Cited

U.S. PATENT DOCUMENTS 6,656,496 B1 * 12/2003 Kilpadi ................... A61L 27/56
                                                            424/448
2013/0274630 A1 * 10/2013 Duesterhoft ......... A61B 5/1477
                                                            600/573

FOREIGN PATENT DOCUMENTS

WO    WO-9741899 A1 * 11/1997    ........... A61K 9/7007

OTHER PUBLICATIONS

Su et al., "Topical application of Antrodia cinnamomea ointment in diabetic wound healing", Life, 2022, 12, 507. (Year: 2022).*

* cited by examiner

*Primary Examiner* — Gina C Justice (57) ABSTRACT

The present invention provides an artificial dressing and a use of the artificial dressing for promoting wound healing. The artificial dressing includes a gelatin and a fungal extract.

5 Claims, 6 Drawing Sheets
(2 of 6 Drawing Sheet(s) Filed in Color)

FIG. 1

| Cross-sectional view | Gelatin 4 mL | Gelatin 2 mL | $2.5*10^{-4}$ mg/mL (B) | $1.9375*10^{-4}$ mg/mL ($B^{\frac{3}{4}}$) | $1.375*10^{-4}$ mg/mL ($B^{\frac{1}{2}}$) | $2.5*10^{-5}$ mg/mL (A) |
|---|---|---|---|---|---|---|
| 50X | | | | | | |
| 100X | | | | | | |
| Pore diameter | 171.53 μm | 54.854 μm | 103.004 μm | 102.717 μm | 97.642 μm | 89.973 μm |

ARTIFICIAL DRESSING AND USE OF ARTIFICIAL DRESSING FOR PROMOTING WOUND HEALING

TECHNICAL FIELD

The present invention relates to an artificial dressing and a use of the artificial dressing for promoting wound healing.

DESCRIPTION OF RELATED ART

Wounds may occur when the skin is injured (for example, scald, trauma, surgery, and contusion), and the types and sizes of the wounds, the patient's nutritional status and age, and the medicine used can affect the process and time of wound healing. In general, wound healing can be divided into 3 phases: (1) inflammatory phase: an inflammatory response occurs at the wound, which promotes the removal of bacteria and necrosis tissue; (2) proliferative phase: granulation tissue proliferation, angiogenesis, epithelialization, and contraction occur at the wound, which reduces the size of the wound; and (3) maturation phase: collagen remolding and capillary regression occur at the wound, which promotes the wound to heal.

In order to accelerate wound healing and reduce wound infection, it is necessary to apply an appropriate dressing to the wound during the wound healing process. Although there are many dressings currently available for promoting wound healing, they are not ideal in terms of therapeutic efficacy and may have problems such as wound adhesion, poor air permeability, poor water absorption, cytotoxicity of the medicine used, and insignificant anti-inflammatory and antibacterial effects.

In order to solve the above problems, those skilled in the art are urgently required to develop a novel artificial dressing to benefit the patients having such a need.

SUMMARY

In view of the above, an object of the present invention is to provide an artificial dressing for promoting wound healing, including a gelatin and a fungal extract.

Another object of the present invention is to provide a use of a composition for preparing an artificial dressing for promoting wound healing. The composition includes a gelatin and a fungal extract.

Another object of the present invention is to provide a use of a composition for preparing an artificial dressing for promoting wound healing. The composition includes a gelatin and a fungal extract, and the fungal extract is applied to an individual with a wound at a frequency of two days.

In one embodiment of the present invention, the artificial dressing has a pore diameter of 54 μm to 172 μm.

In one embodiment of the present invention, the artificial dressing has a porosity of 94% to 96%.

In one embodiment of the present invention, the gelatin has a concentration of 0.025 g/mL to 0.05 g/mL.

In one embodiment of the present invention, the fungal extract has a concentration of 0.25 ppm to 200 ppm.

In one embodiment of the present invention, the fungal extract is an *Antrodia cinnamomea* extract.

In one embodiment of the present invention, the wound healing is wound healing of a diabetic model.

To sum up, the effects of the artificial dressing of the present invention lie in that: the artificial dressing includes a gelatin and a fungal extract, and has a pore diameter of 54 μm to 172 μm and a porosity of 94% to 96% for promoting wound healing, especially, wound healing of a diabetic model. In addition, the structure of the dressing made by adding only a gelatin in the related art tends to disintegrate. The addition of the fungal extract enhances the processability and imparts the antibacterial effect to the artificial dressing.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows the pore diameters of the artificial dressing measured from a cross-sectional view angle, with the magnifications including 50× and 100×.

DETAILED DESCRIPTION OF DISCLOSED EMBODIMENTS

Definition

The numerical values used herein are approximations, and all the experimental data is expressed within 20%, preferably within 10%, and most preferably within 5%.

Example 1. Preparation of Artificial Dressing and Measurement of Pore Diameter and Porosity 0.178 g of a gelatin was weighed in a sample bottle and added with 2 mL of deionized water, and then placed on a magnetic stirrer for stirring (50° C., 600 rpm). After the gelatin was roughly dissolved (about 20 to 30 minutes), the heating temperature was turned off. After the solution cooled down a little, 2 mL of a fungal extract (an *Antrodia cinnamomea* extract was used in this example) was pipetted into the sample bottle and continued to be placed on the magnetic stirrer for stirring (600 rpm). After being stirred roughly evenly (about 10 to 20 minutes), the solution in the sample bottle was sucked into a petri dish with a micropipette, and the petri dish was placed in a −80° C. refrigerator (about 4 to 5 hours) for freezing. Thereafter, the petri dish was taken out of the −80° C. refrigerator, the top cover of the petri dish was opened, and the opening of the petri dish was covered with clean paper and fixed with tape, which was then put into a freeze dryer for freeze drying. The artificial dressing was collected after freeze drying for one day. Next, the prepared artificial dressing was used for measurement of pore diameter and porosity, wherein the porosity was measured using an Autopore-mercury porosimeter. The operation flow of the pore diameter measurement is as follows: the pore diameter in the cross-sectional view of the dressing photographed by a scanning electron microscope is calculated through ImageJ image analysis software. The operation flow of the porosity measurement is as follows: an experimental device using the mercury intrusion method is called a mercury porosimeter, which is a device that applies pressure to a porous object sample placed in a container according to the principle of mercury intrusion method. Since mercury does not wet a general solid, an external pressure needs to be applied to allow mercury to enter the pores. The greater the external pressure, the smaller the radius of the pores that the mercury can enter. The pore diameter distribution and total pore volume can be obtained by obtaining the volume of mercury pressed into the porous object under a series of different pressures by a continuous operation. The experiment results are shown in FIG. 1 to FIG. 3.

Figure 1:
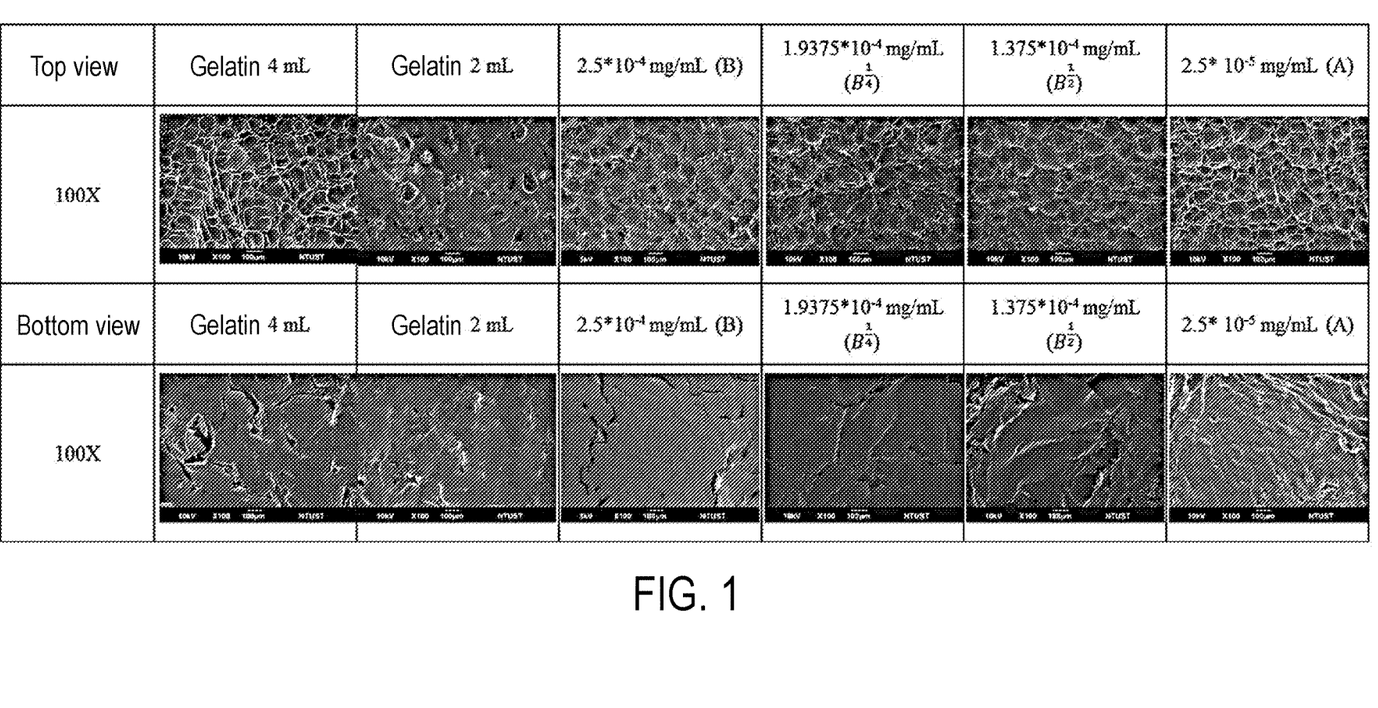
FIG. 1 shows the pore diameters of the artificial dressing measured from top-view and bottom-view angles, with the magnification being 100×.

FIG. 1 and FIG. 2 show the pore diameters of the artificial dressing measured from different angles (including top view, bottom view, and cross-sectional view), and the magnifications include 50× and 100×. It can be seen from FIG. 1 and FIG. 2 that the pore diameter of the artificial dressing can be adjusted when different volumes of gelatin and different concentrations of fungal extract are added. Overall, the artificial dressing of the present invention has a pore diameter of 54 μm to 172 μm. It can be seen from FIG. 1 and FIG. 2 that the thickness of the dressing can be effectively adjusted with different volumes of gelatin. This volume is the volume of deionized water when preparing the gelatin solution, and the volume of the gelatin solution is positively correlated with the thickness of the dressing. The substances added with different concentrations are the medicine concentrations of the fungal (that is, *Antrodia cinnamomea*) extract, and the English letters in the parentheses are the codes given for distinguishing samples in the experiment.

Figure 3:
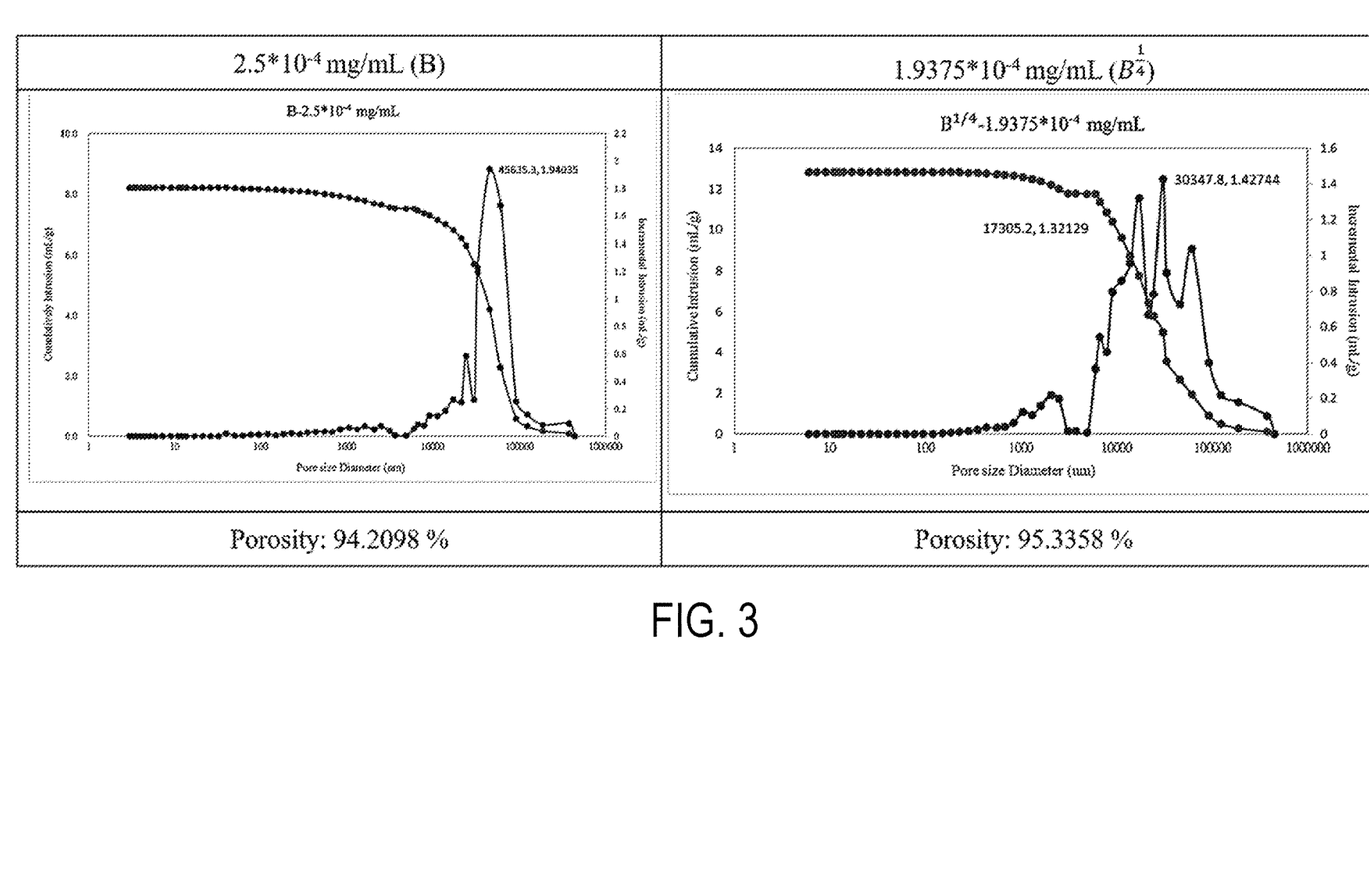
FIG. 3 is a schematic diagram of the measurement results of the porosity of the artificial dressing of the present invention.

FIG. 3 is a schematic diagram of the measurement results of the porosity of the artificial dressing of the present invention. It can be seen from FIG. 3 that the porosity of the artificial dressing can be adjusted when different concentrations of fungal extract are added. Overall, the artificial dressing of the present invention has a porosity of 94% to 96%. The substances added with different concentrations are the medicine concentrations of the fungal (that is, *Antrodia cinnamomea*) extract, and the English letters in the parentheses are the codes given for distinguishing samples in the experiment.

Example 2. Evaluation of Efficacy of Artificial Dressing in Promoting Wound Healing This example explores the efficacy of the artificial dressing of the present invention in promoting wound healing (especially, wound healing of a diabetic model).

First, 6 laboratory mice C57BL/6JNarl (sourced from the National Laboratory Animal Center) were fasted for 6 hours and then anesthetized, and their blood was collected to measure the fasting blood glucose with a blood glucose machine (Bionime Corporation). Then, a medicine for inducing diabetic wound model (that is, 75 mg/kg streptozotocin (STZ), dissolved in pH 4.5 saline sodium citrate and 150 mg/kg STZ-inhibiting organ-protecting medicine nicotinamide (NA) (dissolved in pH 7.4 phosphate buffered saline)) was injected, so as to complete the induction of the first day. The subsequent induction was the same as the first day, and the induction was continued until the fasting blood glucose ≥250 mg/dL, which meant that the diabetic wound model was successfully induced. After confirming that the laboratory mice have been successfully induced into the diabetic wound model, wounds were opened for wound experiment, wherein the wounds of the laboratory mice were divided into four groups, including negative control (NC) group, positive control (PC) group, experimental group 1, and experimental group 2. The negative control group was given 0.178 g of gelatin and 4 mL of deionized water; the positive control group was given the AQUACEL® Foam dressing of ConvaTec, a commercially available foam dressing; the experimental group 1 was given the artificial dressing of the present invention (containing 0.178 g of gelatin, 2 mL of deionized water, and 2 mL of 200 ppm fungal extract); and the experimental group 2 was given the artificial dressing of the present invention (containing 0.178 g of gelatin, 2 mL of deionized water, and 2 mL of 0.25 ppm fungal extract).

Figure 4:
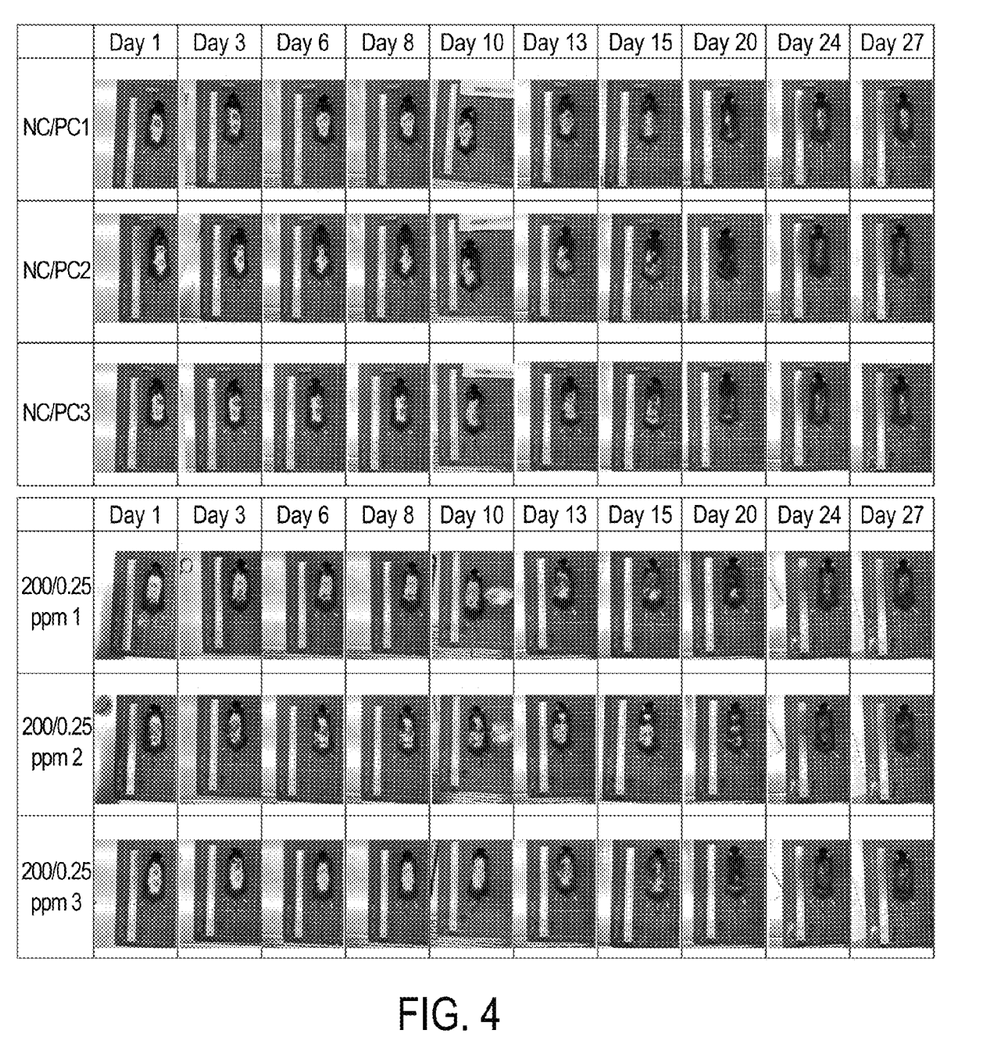
FIG. 4 shows the photographs of records of the wounds in the wound experiment of laboratory mice in each group, wherein NC represents the negative control group, PC represents the positive control group, 200/0.25 ppm respectively represents the wounds of the mice in the experimental group 1 and the experimental group 2, the upper wound in the upper photograph represents the negative control group and the lower wound represents the positive control group, and the upper wound in the lower photograph represents the experimental group 1 and the lower wound represents the experimental group 2.
Figure 5:
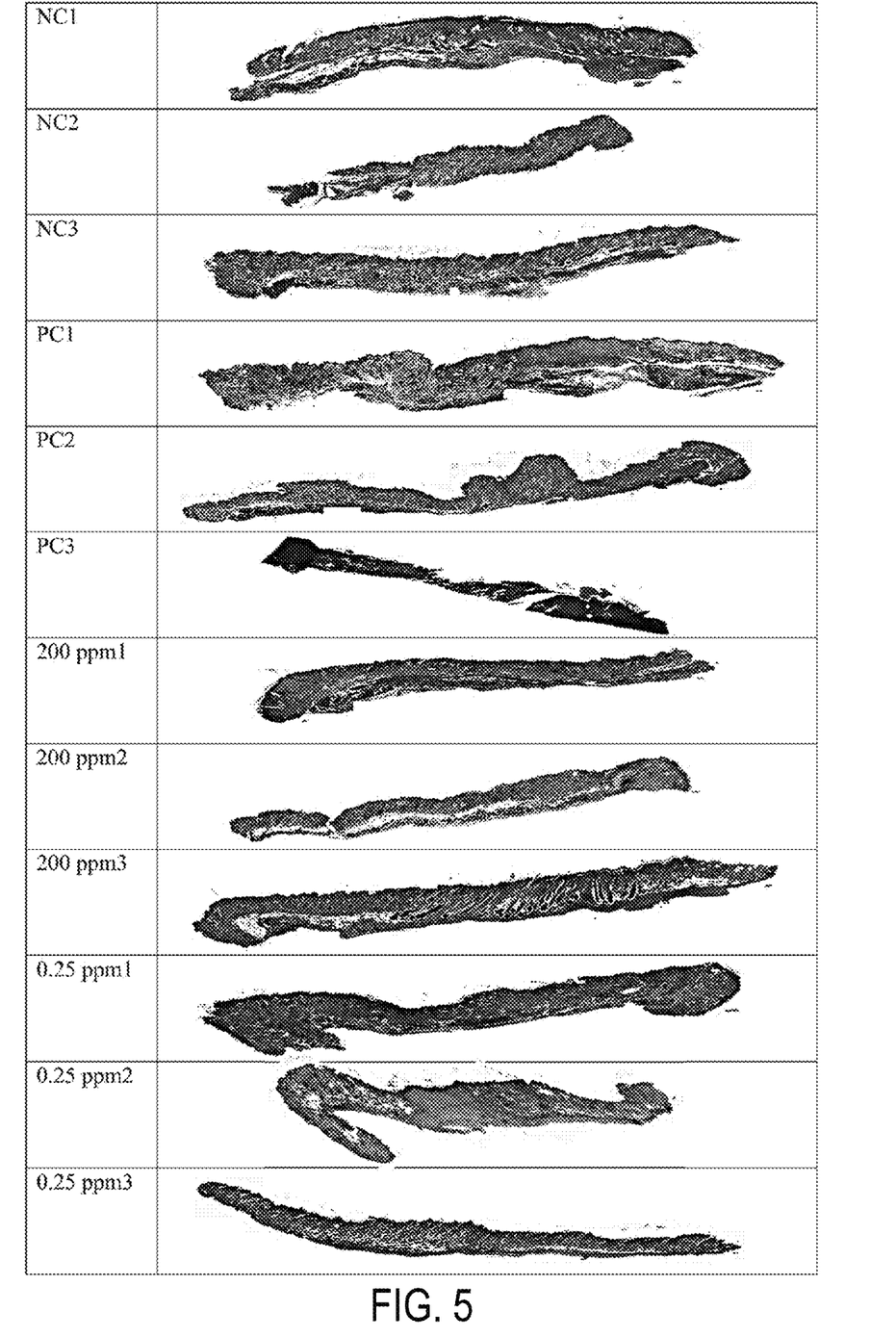
FIG. 5 shows the stained histopathological sections of the wounds in the wound experiment of laboratory mice in each group, wherein NC represents the negative control group, PC represents the positive control group, 200 ppm represents the experimental group 1, and 0.25 ppm represents the experimental group 2's wounds of the mice.

The experiment was repeated three times. First, the laboratory mice in each group were anesthetized with 80 to 160 mg/kg anesthetics (that is, tiletamine and zolazepam (Virbac)), and the hair on their backs was removed and wounds were opened. The wound area was a rectangle of 1 cm×1 cm. 5 mg/kg analgesics (that is, carprofen (Zoetis)) was given to the experimental animals twice a day for the first three days after the wound was opened, and the postoperative condition was recorded. The dressing was changed every two days and the wound was photographed and recorded, and the degree of adhesion of the dressing was evaluated. The dressing was changed continuously for four weeks (28 days) until the wound was completely closed. The photographs of the wounds are shown in FIG. 4. After the wounds were closed, the laboratory mice were sacrificed using 80 to 160 mg/kg anesthetics (that is, tiletamine and zolazepam), 80 to 160 mg/kg muscle relaxant (that is, xylazine (Health-Tech Pharmaceutical Co., Ltd.)), and 5 mg/kg analgesics (that is, carprofen). After the animals were sacrificed, the required tissue sections were removed and sent to the Taipei Institute of Pathology for pathological sections. After the sections were retrieved, the sections were photographed with an optical microscope and analyzed by ImageJ image analysis software. The stained histopathological sections are shown in FIG. 5.

The positive control group in this example used the commercially available AQUACEL® Foam dressing of ConvaTec, which had slight wound adhesion on the inner layer. Therefore, when the dressing was replaced, the wound area expanded. Other experimental groups also had some wound expansions, which may be caused by the experimental animals scratching or biting the wounds of themselves or each other.

During the whole animal experiment, the body weight, appetite, and activity of the experimental animals were not much different from those before the experiment whether they were in the early stage when STZ was applied to establish the diabetic wound model, or in the later stage when the wound experiment was carried out. Thus, it can be seen that the experiment carried out did not cause too much physiological load to the experimental animals, and the experiment was completed in a stable state.

The results of the area changes of the wounds of the laboratory mice in each group related to this example are shown in Table 1, Table 2, and FIG. 6 below, wherein FBG represents fasting blood glucose.

TABLE 1

| Wound area unit: cm² | | NC | | | PC | | |
|---|---|---|---|---|---|---|---|
| | | 1 | 2 | 3 | 1 | 2 | 3 |
| Day 1 | Shave | | | | | | |
| Day 2 | Open wound, analgesics | 1.1 | 0.621 | 0.661 | 0.650 | 0.506 | 0.646 |
| Day 3 | Analgesics | | | | | | |
| Day 4 | Change dressing, analgesics | 1.075 | 0.473 | 0.653 | 0.840 | 0.732 | 0.681 |
| Day 7 | Change dressing | 0.161 | 0.138 | 0.225 | 0.540 | 0.734 | 0.711 |
| Day 9 | Change dressing | 0.350 | 0.130 | 0.192 | 0.806 | 0.624 | 0.584 |
| Day 11 | Change dressing | 0.208 | 0.077 | 0.082 | 0.446 | 0.265 | 0.436 |
| Day 14 | Change dressing | 0.072 | 0.081 | 0.038 | 0.138 | 0.114 | 0.178 |
| Day 16 | Change dressing | 0.096 | 0.059 | 0.034 | 0.019 | 0.065 | 0.073 |
| Day 18 | Observe | 0.059 | 0.030 | 0.018 | 0.003 | 0.034 | 0.039 |
| Day 21 | Observe | 0.032 | 0.016 | 0.005 | 0 | 0.017 | 0.019 |
| Day 23 | Observe | 0.011 | 0.007 | 0 | 0 | 0.005 | 0.007 |
| Day 25 | Observe, shave | 0.004 | 0 | 0 | 0 | 0 | 0 |
| Day 28 | Sacrifice | 0 | 0 | 0 | 0 | 0 | 0 |
| | FBG (mg/dL) | 303 | 312 | 308 | 317 | 328 | 321 |

TABLE 2

| Wound area unit: cm² | | 200 ppm | | | 0.25 ppm | | |
|---|---|---|---|---|---|---|---|
| | | 1 | 2 | 3 | 1 | 2 | 3 |
| Day 1 | Shave | | | | | | |
| Day 2 | Open wound, analgesics | 0.675 | 0.685 | 0.753 | 0.619 | 0.621 | 0.805 |
| Day 3 | Analgesics | | | | | | |
| Day 4 | Change dressing, analgesics | 0.676 | 0.662 | 0.745 | 0.594 | 0.456 | 0.805 |
| Day 7 | Change dressing | 0.416 | 0.428 | 0.305 | 0.333 | 0.354 | 0.400 |
| Day 9 | Change dressing | 0.327 | 0.367 | 0.398 | 0.203 | 0.293 | 0.355 |
| Day 11 | Change dressing | 0.150 | 0.415 | 0.141 | 0.345 | 0.211 | 0.466 |
| Day 14 | Change dressing | 0.050 | 0.132 | 0.037 | 0.114 | 0.171 | 0.145 |
| Day 16 | Change dressing | 0.134 | 0.062 | 0.045 | 0.081 | 0.172 | 0.150 |
| Day 18 | Observe | 0.108 | 0.048 | 0.029 | 0.067 | 0.131 | 0.119 |
| Day 21 | Observe | 0.072 | 0.027 | 0.006 | 0.042 | 0.104 | 0.084 |
| Day 23 | Observe | 0.034 | 0.008 | 0 | 0.019 | 0.078 | 0.059 |
| Day 25 | Observe, shave | 0.011 | 0 | 0 | 0.003 | 0.034 | 0.027 |
| Day 28 | Sacrifice | 0 | 0 | 0 | 0 | 0 | 0 |
| | FBG (mg/dL) | 303 | 312 | 308 | 317 | 328 | 321 |

Figure 6:
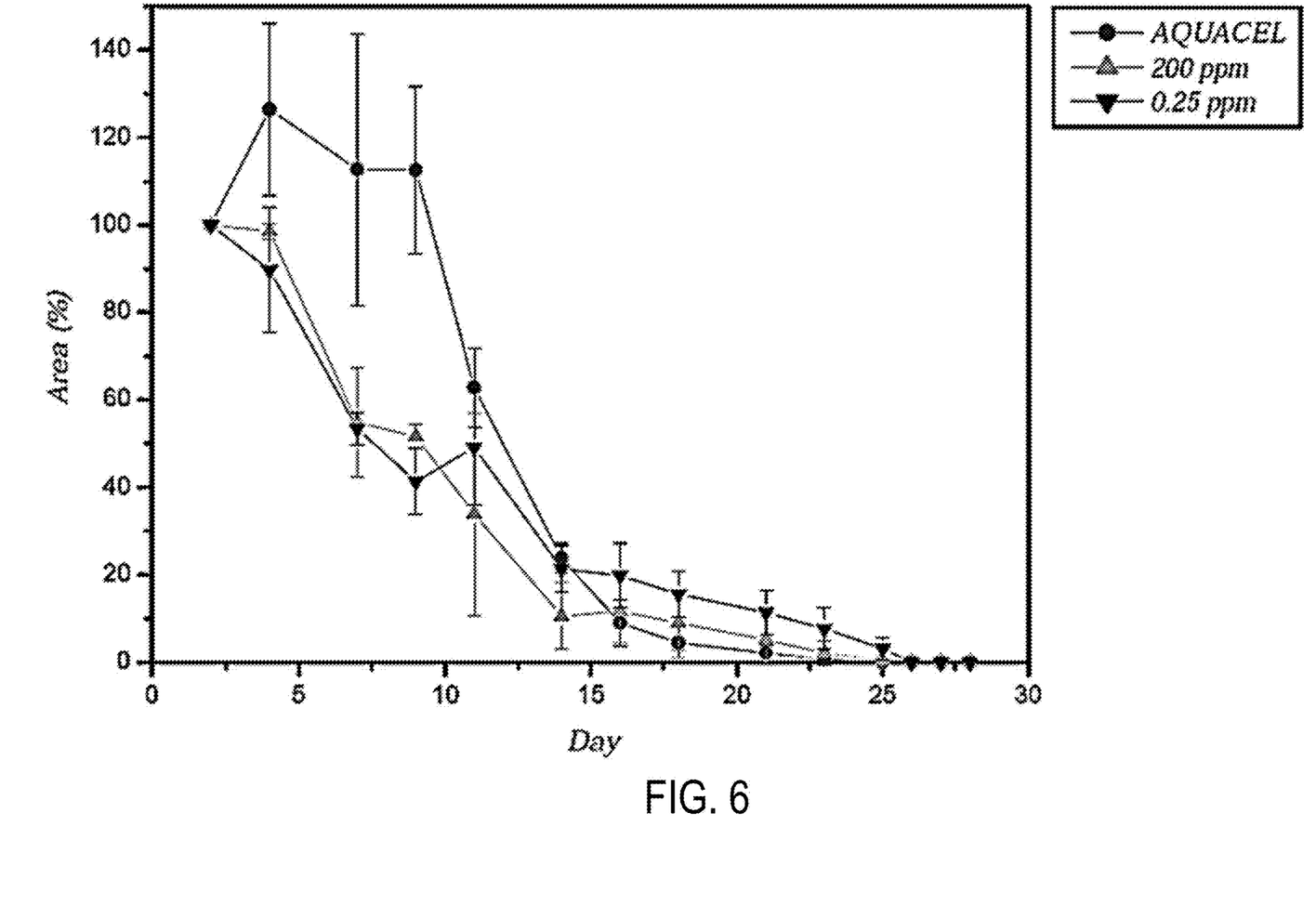
FIG. 6 shows the area changes of the wounds in the wound experiment of laboratory mice in each group, wherein AQUACEL represents the positive control group, 200 ppm represents the experimental group 1, and 0.25 ppm represents the experimental group 2's wounds of the mice.

As can be seen from the results in Table 1, Table 2, and FIG. 6, the two experimental groups given with fungal extracts at 200 ppm and 0.25 ppm both showed the maximum healing speed from the fourth to the seventh days, whereas the PC group showed the maximum healing speed from the ninth to the eleventh days, which shows that the fungal extract experimental group had an earlier wound healing effect than the commercially available positive control group.

On the eleventh to the fourteenth days, the three experimental groups all showed healing speeds with the second largest slope, followed by a gradual wound closing process. It is inferred that this period may be an important period of wound healing.

The 200 ppm experimental group 1 had the first fully wound-closed mouse on the twenty-third day, the second one appeared on the twenty-fifth day, and the last one had the wound fully closed on the twenty-eighth day. The 0.25 ppm experimental group 2 had three fully wound-closed mice on the twenty-eighth day. From the wound closing speed in the end stage, it can be seen that there is a slight difference in the wound healing speed between the two fungal extract experimental groups. The high concentration of 200 ppm is better than the low concentration of 0.25 ppm.

The results of this example show that, compared with the positive control group and the negative control group, the wound healing speed of the wound groups (that is, the experimental group 1 and the experimental group 2) applied with the artificial dressing of the present invention is significantly improved.

To sum up, the artificial dressing of the present invention includes a gelatin and a fungal extract, and has a pore diameter of 54 μm to 172 μm and a porosity of 94% to 96% for promoting wound healing, especially, wound healing of a diabetic model. In addition, the structure of the dressing made by adding only a gelatin in the related art tends to disintegrate. The addition of the fungal extract enhances the processability and imparts the antibacterial effect to the artificial dressing.

Nevertheless, the above description is exemplary rather than restrictive. Any equivalent modifications or changes that do not depart from the spirit and scope of the present invention shall be included in the appended claims.

What is claimed is:

1. An artificial dressing, comprising a gelatin stirred with a fungal extract, wherein the artificial dressing has a pore diameter of 54 μm to 172 μm and a porosity of 94% to 96%;
    wherein the artificial dressing is formed of a concentration of 0.025 g/mL to 0.05 g/mL of the gelatin and a concentration of 0.25 ppm to 200 ppm of the fungal extract;
    wherein the artificial dressing promotes wound healing; and
    wherein the fungal extract is an *Antrodia cinnamomea* extract.

2. The artificial dressing according to claim 1, wherein the wound healing is wound healing of a diabetic model.

3. A use of a composition comprising a gelatin and a fungal extract in preparation of an artificial dressing that promotes wound healing, wherein the artificial dressing comprises the gelatin stirred with the fungal extract, wherein the artificial dressing has a pore diameter of 54 μm to 172 μm and a porosity of 94% to 96%;
    wherein the artificial dressing is prepared by following steps:
    adding deionized water into the gelatin, and the gelatin is dissolved to have a concentration of 0.025 g/mL to 0.05 g/mL;
    adding a concentration of 0.25 ppm to 200 ppm of the fungal extract to be stirred with the gelatin, wherein the fungal extract is an *Antrodia cinnamomea* extract; and
    performing freezing and drying to form the artificial dressing.

4. The use of the composition according to claim 3, wherein the wound healing is wound healing of a diabetic model.

5. A use of an artificial dressing in promotion of wound healing, wherein the the artificial dressing comprises a gelatin stirred with a fungal extract, and the artificial dressing is applied to an individual with a wound at a frequency of two days, wherein the artificial dressing has a pore diameter of 54 μm to 172 μm and a porosity of 94% to 96%;
    wherein the artificial dressing is prepared by following steps:
    adding deionized water into the gelatin, and the gelatin is dissolved to have a concentration of 0.025 g/mL to 0.05 g/mL;
    adding a concentration of 0.25 ppm to 200 ppm of the fungal extract to be stirred with the gelatin, wherein the fungal extract is an *Antrodia cinnamomea* extract; and
    performing freezing and drying to form the artificial dressing.

* * * * *